(12) United States Patent
Bui et al.

(10) Patent No.: US 9,474,710 B2
(45) Date of Patent: Oct. 25, 2016

(54) MASCARA COMPOSITION

(71) Applicant: L'OREAL, Paris (FR)

(72) Inventors: Hy Si Bui, Piscataway, NJ (US);
Christopher Pang, New York, NY (US); Kavita Patel, East Windsor, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/636,395

(22) Filed: Mar. 3, 2015

(65) Prior Publication Data

US 2016/0256378 A1 Sep. 8, 2016

(51) Int. Cl.
*A61K 8/92* (2006.01)
*A61Q 1/10* (2006.01)
*A61K 8/91* (2006.01)
*A61K 8/81* (2006.01)

(52) U.S. Cl.
CPC ............. *A61K 8/927* (2013.01); *A61K 8/8147* (2013.01); *A61K 8/91* (2013.01); *A61Q 1/10* (2013.01)

(58) Field of Classification Search
None
See application file for complete search history.

(56) References Cited

U.S. PATENT DOCUMENTS

| 7,431,919 B2 | 10/2008 | Travkina et al. |
| 8,865,193 B2 | 10/2014 | Wolff et al. |
| 2003/0235553 A1* | 12/2003 | Lu ............................ A61K 8/894 424/70.122 |
| 2008/0014164 A1 | 1/2008 | Jacquier |
| 2009/0142289 A1* | 6/2009 | Arditty .................... A61Q 1/10 424/70.7 |
| 2010/0028284 A1 | 2/2010 | Atis et al. |
| 2011/0020261 A1 | 1/2011 | Bui et al. |
| 2012/0207801 A1 | 8/2012 | Sandstrom |
| 2012/0276034 A1 | 11/2012 | Zheng et al. |
| 2013/0039874 A1 | 2/2013 | Li et al. |
| 2014/0286893 A1 | 9/2014 | Alden-Danforth et al. |

FOREIGN PATENT DOCUMENTS

KR    10-0425353 B1    3/2004

OTHER PUBLICATIONS

U.S. Appl. No. 14/636,411, filed Mar. 3, 2015, Bui, et al.
International Search Report and Written Opinion, dated May 30, 2016, in PCT/US2016/018588 (12 pages).

* cited by examiner

*Primary Examiner* — Robert A Wax
*Assistant Examiner* — Randeep Singh
(74) *Attorney, Agent, or Firm* — Oblon, McClelland, Maier & Neustadt, L.L.P.

(57) ABSTRACT

A mascara composition including at least one olefin/acrylate grafted polymer and at least one acrylates copolymer. The ratio of the weight amount of the olefin/acrylate grafted polymer to the weight amount of the acrylates copolymer in the mascara composition is preferably from about 0.85 to about 4.5.

11 Claims, 5 Drawing Sheets

MASCARA COMPOSITION

TECHNICAL FIELD

The present invention relates to a cosmetic composition for keratinous materials such as keratin fibers. The cosmetic composition is preferably a mascara composition for eyelashes.

BACKGROUND

Mascara compositions are commonly used to enhance the appearance of eyelashes. Conventional mascara compositions generally use waxes to form crystalline network structures to impart curl, volume, length, thickness, and/or colors to eyelashes. However, mascara compositions including large amount of waxes tend to become less resistant to oil and/or sebum, causing smearing, flaking, and/or color transferring after wearing for a certain amount of time.

Thus, there is a need for a long-lasting mascara composition which imparts an enhanced degree of curl, volume, length, thickness, and/or color for an extended period of time.

Accordingly, one aspect of the present invention is a mascara composition which is able to address or overcome at least the aforementioned problems associated with the conventional mascara compositions. In particular, one aspect of the present invention is directed to a mascara composition which imparts an enhanced appearance to the eyelashes for an extended period of time. Another aspect of the present invention is directed to a method of making up eyelashes to enhance physical appearance of the eyelashes.

SUMMARY

According to preferred embodiments of the present invention, a mascara composition includes at least one olefin/acrylate grafted polymer and at least one acrylates copolymer. Preferably, the ratio of the weight amount of the olefin/acrylate grafted polymer to the weight amount of the acrylates copolymer in the mascara composition is from about 0.85 to about 4.5.

According to preferred embodiments of the present invention, the mascara composition further includes at least one wax. Preferably, the amount of the wax, if present, is about 10% by weight or less relative to the total weight of the mascara composition.

According to preferred embodiments of the present invention, a process of making a mascara composition includes mixing at least one olefin/acrylate grafted polymer and at least one acrylates copolymer until dissolution. Preferably, the ratio of the weight amount of the olefin/acrylate grafted polymer to the weight amount of the acrylates copolymer mixed in the mascara composition is from about 0.85 to about 4.5.

According to preferred embodiments of the present invention, a method of making up eyelashes includes applying a mascara composition including at least one olefin/acrylate grafted polymer and at least one acrylates copolymer onto eyelashes in an amount sufficient to makeup eyelashes. Preferably, the ratio of the weight amount of the olefin/acrylate grafted polymer to the weight amount of the acrylates copolymer in the mascara composition is from about 0.85 to about 4.5.

According to preferred embodiments of the present invention, a method of increasing curl of eyelashes includes applying a mascara composition including at least one olefin/acrylate grafted polymer and at least one acrylates copolymer onto eyelashes in an amount sufficient to increase curl of the eyelashes. Preferably, the ratio of the weight amount of the olefin/acrylate grafted polymer to the weight amount of the acrylates copolymer in the mascara composition is from about 0.85 to about 4.5.

DETAILED DESCRIPTION

Figure 1A:
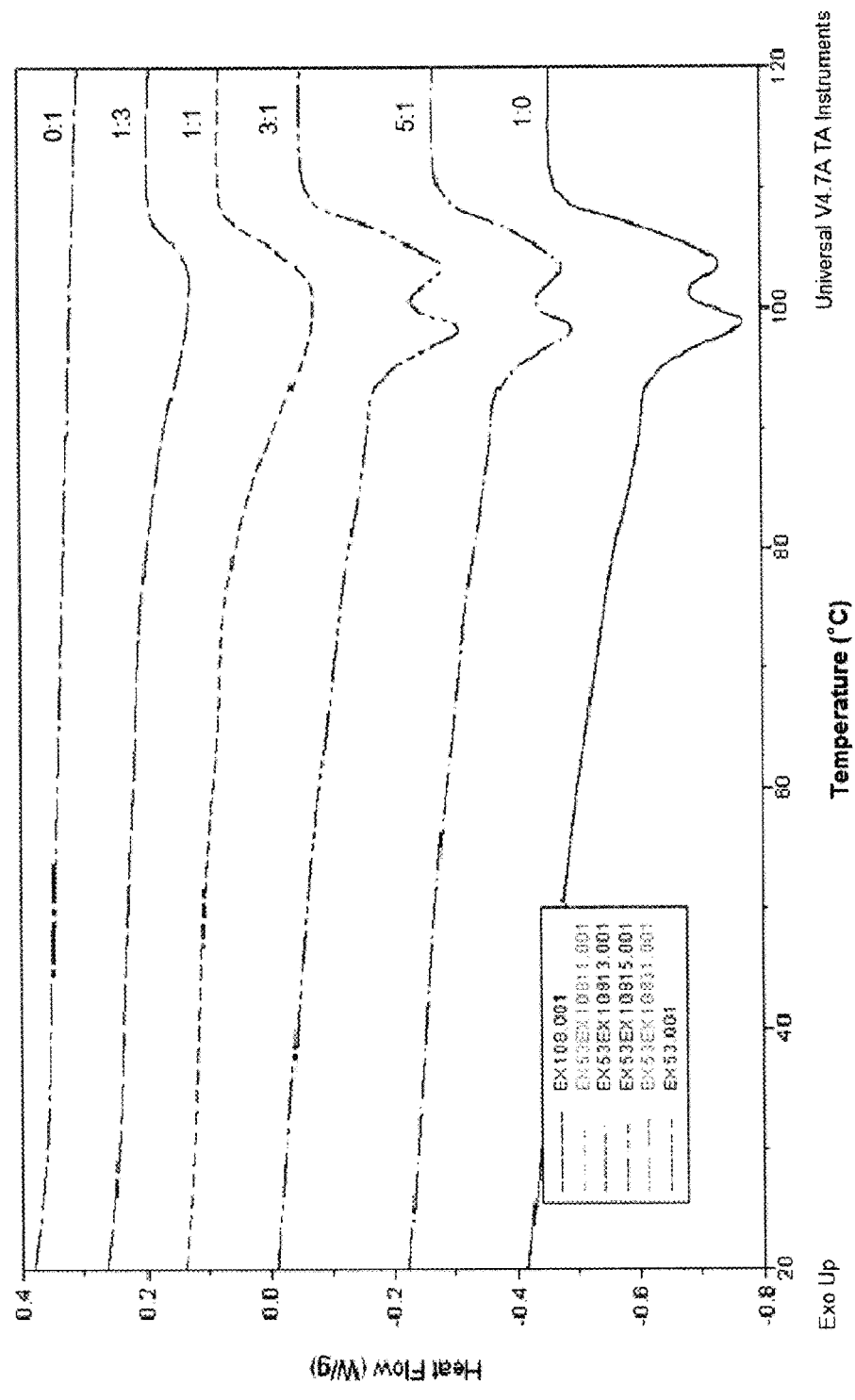
FIG. 1A is a graph showing the DSC measurement result when heating mixtures of Syntran® EX108 and Syntran® EX 53 with various mixing ratios. The mixing ratio indicates a weight ratio of (Syntran® EX108):(Syntran® EX 53).

Unless otherwise indicated, all numbers expressing quantities of ingredients and/or reaction conditions are to be understood as being modified in all instances by the term "about." Accordingly, unless indicated to the contrary, the numerical parameters set forth in the following specification and attached claims are approximations that may vary depending upon the desired properties sought to be obtained by the present invention.

As used herein, the expression "at least one" means one or more and thus includes individual components as well as mixtures/combinations.

As used herein, the singular forms "a," "an," and "the" are intended to include the plural forms as well, unless the context clearly indicates otherwise. It will further understood that the terms "comprising," "including," and variants thereof, when used in this specification, specify the presence of stated features, elements, and/or components, but do not preclude the presence or addition of one or more other features, elements, components, and/or groups thereof.

As used herein, "mascara" and "mascara composition" mean a composition that is intended to be applied to keratinous materials, preferably keratin fibers, in particular eyelashes and/or eyebrows, further in particular eyelashes.

As used herein, "keratinous materials" include, but are not limited to, skin, nail, living keratin fibers such as head hair, eyelashes, and eyebrows, and non-living keratin fibers such as swatches, extensions, and false eyelashes. The living and non-living keratin fibers include any mammalian hair, including human hair.

As used herein, "waterproof" refers to the ability to repel water and permanence with respect to water. Waterproof properties may be evaluated by any method known in the art for evaluating such properties. For example, a mascara composition may be applied to false eyelashes, which may then be placed in water for a certain amount of time, such as, for example, 20 minutes. Upon expiration of the pre-ascertained amount of time, the false eyelashes may be removed from the water and passed over a material, such as, for example, a sheet of paper. The extent of residue left on the material may then be evaluated and compared with other compositions, such as, for example, commercially available compositions. Similarly, for example, a composition may be applied to skin, and the skin may be submerged in water for a certain amount of time. The amount of composition remaining on the skin after the pre-ascertained amount of time may then be evaluated and compared. For example, a composition may be waterproof if a majority of the product is left on the wearer, e.g., eyelashes, skin, etc. In a preferred embodiment of the present invention, little or no composition is transferred from the wearer.

As used herein, a "long-lasting" composition refers to compositions where appearance of the composition, including a film formed by the composition, remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the appearance of the composition after an extended period of time. For example, the appearance of a composition may be evaluated immediately following application to hair, skin or lips and these characteristics may then be re-evaluated and compared after a certain amount of time. Further, these characteristics may be evaluated with respect to other compositions, such as commercially available compositions.

The mascara composition and methods of the present invention can comprise, consist of, or consist essentially of the essential elements and limitations of the invention described herein, as well as any additional or optional ingredients, components, or limitations described herein or otherwise useful in personal care compositions intended for application to keratinous materials.

For purposes of the mascara composition of the present invention, the basic and novel property of a mascara composition "consisting essentially of" at least one olefin/acrylate grafted polymer and at least one acrylates copolymer is to provide the eyelashes a spiking appearance for an extended period of time.

(Olefin/Acrylate Grafted Polymer)

According to preferred embodiments of the present invention, the mascara composition includes at least one olefin/acrylate grafted polymer. According to one of ordinary skill in the art, the term "olefin" refers to an alkene, which may be any aliphatic hydrocarbon whose molecules contain at least one carbon-carbon double bond. As used herein, the term "acrylate" refers to, for example, acrylic acid or any ester of acrylic acid, with the formula $CH_2C(R^1)COOR^2$, in which $R^1$ and $R^2$ can be hydrogen or an organic group having any number of carbon atoms. For example, $R^1$ and $R^2$ may be, but not limited to, methyl, ethyl, butyl, lauryl, and stearyl groups. The term "grafted" means, for example, physical entanglement of polymer chains and covalent grafting. The grafting may be sufficient to provide a uniform polymer emulsion with a single glass transition temperature ($T_g$) and an ability to withstand thermal and chemical attack without dissociation.

The olefin/acrylate grafted polymer that is preferably utilized in the mascara composition may be a semi-crystalline polymer. As used herein, "semi-crystalline polymer" refers to polymers that exist as viscous liquids at temperatures above the melting point of the crystals. Upon cooling, crystals nucleate and grow to fill the available volume. In a semi-crystalline polymer, some fraction of the polymer may remain un-crystallized, or, amorphous, when the polymer is cooled to room temperature. The amorphous polymer may become trapped between the growing crystals. As a result of the highly entangled (or "grafted") nature of the polymer chains, the movement of the amorphous polymer may become restricted.

Any types of olefin/acrylate grafted polymers that are cosmetically or dermatologically acceptable may be utilized in the present invention. As used herein, "cosmetically acceptable" or "dermatologically acceptable" is intended to mean that a composition is suitable for use in contact with human tissues such as keratinous materials and mucous membranes without undue toxicity, incompatibility, instability, and/or allergic response.

The olefin/acrylate grafted polymer may have a relatively low glass transition temperature, such as less than about 0° C. In some embodiments, the glass transition temperature of the olefin/acrylate grafted polymer is less than about −0.5° C., preferably less than about −5° C. The olefin/acrylate grafted polymer may have a glass transition temperature of from about −20° C. to about −0.5° C., preferably from about −10° C. to about −5° C., including all ranges and subranges therebetween.

When the olefin/acrylate grafted polymer and optionally a surfactant are dispersed in water, the dispersion may have a pH value of from about 7 to about 12, preferably from about 8 to about 10, including all ranges and subranges therebetween.

In some embodiments, the olefin/acrylate grafted polymer may be a commercially available olefin/acrylate grafted polymer dispersion, such as Syntran® EX 108 (INCI name: olefin/acrylate grafted polymer (and) sodium laureth sulfate (and) C12-15 Sec-Pareth 15) from Interpolymer. Syntran® EX 108 is available in the form of a dispersion, a latex, or an emulsion, in which an olefin/acrylate grafted polymer is dispersed in water. Syntran® EX 108 is known to include about 62% by weight of water, about 33% by weight in solid of olefin/acrylate grafted polymer, about 1% by weight of sodium laureth sulfate, and about 1% by weight of C12-15 Sec-Pareth 15. Syntran® EX 108 may have a glass transition temperature of about −6.32° C. Other non-limited examples of commercially available olefin/acrylate grafted polymer that are preferably utilized in the mascara composition include Syntran® PC5205, Syntran® PC5208, and Syntran® PC5227 from Interpolymer.

The olefin/acrylate grafted polymers that are preferably used in the present invention may be those disclosed in U.S. Pat. No. 8,865,193, contents of which are incorporated herein by reference in its entirety.

The amount of the olefin/acrylate grafted polymer(s) is preferably more than about 0.5% by weight, more preferably at least about 1% by weight, relative to the total weight of the mascara composition. Preferably, the mascara composition includes the olefin/acrylate grafted polymer(s) in an amount of from about 1% to about 15% by weight, more preferably from about 2% to about 10% by weight, relative to the total weight of the mascara composition, including all ranges and subranges therebetween.

When the mascara composition includes Syntran® EX 108, the amount of Syntran® EX 108 may be from about 3 to about 50% by weight, preferably from about 6 to about 35% by weight, more preferably from about 10 to about 22% by weight, relative to the total weight of the mascara composition, including all ranges and subranges therebetween.

(Acrylates Copolymer)

According to preferred embodiments of the present invention, the mascara composition includes an acrylates copolymer. Any types of acrylates copolymers that are cosmetically and dermatologically acceptable may be utilized in the present invention.

According to one of ordinary skill in the art, the acrylates copolymer may be a polymer formed from at least two monomers of, for example, acrylic acid, methacrylic acid, and esters and amides of acrylic acid or methacrylic acid, and may have a formula of $(-CH_2-CH(COOR)-)_n$, in which R can be hydrogen or an organic group having any number of carbon atoms, and n can be any integer of 2 or greater, preferably about 50 or greater, preferably about 100 or greater. As used herein, the term "(meth)acrylate(s)" is intended to mean acrylate(s) and/or methacrylate(s). For the purpose of the present invention, preferable examples of acrylate monomers from which the acrylates copolymer is prepared may include, but are not limited to, (meth)acrylate, methyl(meth)acrylate, ethyl(meth)acrylate, propyl(meth)acrylate, butyl(meth)acrylate, isobutyl(meth)acrylate, hydroxypropyl methacrylate, and hydroxyethyl methacrylate. Particularly suitable monomers are butyl acrylate, methylmethacrylate, and methacrylic acid.

The acrylates copolymer may have a relatively high glass transition temperature, such as about 0° C. or higher. In some embodiments, the glass transition temperature of the acrylates copolymer may be greater than about 5° C., preferably greater than about 10° C., more preferably greater than about 14° C. The acrylates copolymer may have a glass transition temperature of from about 0° C. to about 30° C., preferably from about 5° C. to about 25° C., more preferably from about 10° C. to about 20° C., including all ranges and subranges therebetween.

When the acrylates copolymer and optionally a surfactant are dispersed in water, the dispersion may have a pH value of from about 6 to about 9, preferably from about 7 to about 8, including all ranges and subranges therebetween.

In some embodiments, the acrylates copolymer may be derived from a commercially available acrylates copolymer dispersion, such as Syntran® EX 53 (INCI name: acrylates copolymer (and) butylene glycol (and) sodium laureth sulfate) from Interpolymer. Syntran® EX 53 is commercially available in the form of a dispersion, a latex, or an emulsion. Syntran® EX 53 is known to include about 56.5% by weight of water, about 39.5% by weight in solid of acrylates copolymer, 1.5% by weight of butylene glycol, and 1% of sodium laureth sulfate. Other non-limited examples of commercially available acrylates copolymer that are preferably utilized in the mascara composition include Syntran® 5190 and Syntran® 5205 from Interpolymer.

The acrylates copolymers that are preferably used in the present invention may be those disclosed in U.S. Pat. No. 8,865,193, contents of which are incorporated herein by reference in its entirety.

The amount of the acrylates copolymer(s) in the mascara composition is preferably more than about 0.1% by weight, more preferably at least about 0.5% by weight, relative to the total weight of the mascara composition. Preferably, the mascara composition includes the acrylates copolymer(s) in an amount of from about 1% to about 10% by weight, more preferably from about 2% to about 8% by weight, relative to the total weight of the mascara composition, including all ranges and subranges therebetween.

When the mascara composition includes Syntran® EX 53, the amount of Syntran® EX 53 may be from about 2.5 to about 30% by weight, preferably from about 5 to about 20% by weight, relative to the total weight of the mascara composition, including all ranges and subranges therebetween.

Although not intended to be bound by any theories, it is currently believed that a combination of the olefin/acrylate grafted polymer and the acrylates copolymer contributes to form a crystalline structure in the mascara composition, which provides sufficient hardness and separation properties while maintaining good sebum and water resistance. During the formation of a film on the keratinous materials, the olefin/acrylate grafted polymer and the acrylates copolymer may form crystalline network patterns different from those formed by waxes. The crystalline network patterns formed by the olefin/acrylate grafted polymer and the acrylates copolymer may have the same or substantially similar effects as those formed by waxes. By controlling the ratio of the olefin/acrylate grafted polymer and the acrylates copolymer, desired crystalline-network-forming effects may be obtained.

The ratio of the weight amount of olefin/acrylate grafted polymer to the weight amount of acrylates copolymer contained in the mascara composition is: preferably about 0.85 or greater, about 1 or greater, about 1.5 or greater, and particularly preferably about 2 or greater; and preferably about 4.5 or less, preferably about 4 or less, and particularly preferably about 3 or less. Preferably, the ratio of the weight amount of olefin/acrylate grafted polymer to the weight amount of acrylates copolymer contained in the mascara composition is from about 0.85 to about 4.5, including all ranges and subranges therebetween.

When the mascara composition includes Syntran® EX 108 and Syntran® EX 53, Syntran® EX 108 and Syntran® EX 53 are preferably mixed in a weight ratio of from about 1:1 to about 5:1, more preferably from about 2:1 to about 4:1, including all ranges and subranges therebetween. Particularly preferred embodiments of the present invention may be prepared by mixing Syntran® EX 108 and Syntran® EX 53 in a weight ratio of from about 2:1 to about 3:1, including all ranges and subranges therebetween.

(Wax)

According to some embodiments of the present invention, the mascara composition may further optionally include a wax. If present, the amount of wax may be up to 50% by weight relative to the total weight of the mascara composition. Preferably, the amount of wax, if present, is about 10% by weight or less, 5% by weight or less, or 2% by weight or less, of the total weight of the mascara composition. The combination of the olefin/acrylate grafted polymer and the acrylates copolymer may render optional the inclusion of waxes. In a particularly preferred embodiment, the mascara composition contains no wax.

As used herein, "wax" is intended to mean a lipophilic fatty compound that is solid at room temperature (about 25° C.) and atmospheric pressure (760 mmHg, i.e., 105 Pa), which undergoes a reversible solid/liquid change of state and which has a melting point of greater than 30° C., and in some embodiments, greater than about 55° C. up to about 120° C. or even as high as about 200° C. In the present invention, any waxes that are cosmetically and dermatologically acceptable may be utilized.

A variety of waxes may be useful, including waxes of animal origin, waxes of plant origin, waxes of mineral origin and waxes of synthetic origin. Examples of waxes of animal origin include beeswaxes, lanolin waxes and Chinese insect waxes.

Examples of waxes of plant origin include rice waxes, carnauba wax, candelilla wax, ouricurry wax, cork fiber waxes, sugar cane waxes, Japan waxes, sumach wax and cotton wax.

Examples of waxes of mineral origin include paraffins, microcrystalline waxes, montan waxes and ozokerites.

Examples of waxes of synthetic origin include polyolefin waxes, e.g., polyethylene waxes, waxes obtained by Fischer-Tropsch synthesis, waxy copolymers and their esters, and silicone and fluoro waxes.

Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or non-linear fatty chain, hydrogenated sunflower oil, hydrogenated castor oil, hydrogenated copra oil, hydrogenated lanolin and hydrogenated palm oils.

The waxes may be used alone or in combination with different kind(s) of waxes. In some embodiments, the mascara composition may include at least two or at least three waxes.

The mascara composition of the present invention may include wax(es) from about 0% to about 15% by weight, preferably from about 0% to about 10% by weight, more preferably from about 0% to about 8% by weight, relative to the total weight of the mascara composition.

According to preferred embodiments of the present invention, the amount of wax(es) may be less than about 10% by weight, preferably less than about 7.5% by weight, relative to the total weight of the mascara composition. The amount of wax in the mascara composition of the present invention may be, for example, about 40%, preferably about 50%, or more preferably about 55% less than the amount of wax(es) contained in conventional mascara compositions. In a particularly preferred embodiment, the mascara composition contains no wax.

(Surfactant)

According to the present invention, the mascara composition may further optionally include a surfactant. Any surfactants, including anionic, nonionic, amphoteric, and cationic, surfactants, may be used in the present invention, as long as the surfactant is cosmetically or dermatologically acceptable. The surfactant may be used either singly or in combination two or more thereof.

In one embodiment, the mascara composition may include sodium laureth sulfate.

If present, the amount of the surfactant may be from about 0.5 to about 50% by weight, preferably from about 3 to about 40% by weight, more preferably from about 5 to about 30% by weight, relative to the total weight of the mascara composition, including all ranges and subranges therebetween.

(Colorants)

According to the present invention, the mascara compositions may optionally include at least one colorant. Suitable colorants include, but are not limited to, pigments, dyes such as liposoluble dyes, nacreous pigments, and pearling agents. Typically, when the composition contains colorants, the composition may be used as a mascara composition. Alternatively, when the composition does not contain colorants, it is a clear or transparent composition which can be used as a basecoat (or topcoat) prior to (or after) application of a mascara composition to keratinous materials. However, it is possible that topcoats or basecoats could contain colorants, and/or that a mascara composition could contain little or no colorant.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration of up to 20% by weight of the total weight of the mascara composition, such as from about 0.0001% to about 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, is in the composition in a concentration of up to 50% by weight relative to the total weight of the mascara composition, such as from about 0.1% to about 20% by weight, preferably from about 0.1% to about 15% by weight, including all ranges and subranges therebetween.

Representative pigments which may be used according to the present invention include white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum. If present, the pigments may be in the mascara composition in a concentration of up to 50% by weight of the total weight of the mascara composition, such as from about 0.5% to about 40% by weight, and further such as from about 2% to about 30% by weight, including all ranges and subranges therebetween. In the case of certain products, the pigments, including nacreous pigments, may, for example, represent up to about 50% by weight of the mascara composition.

(Additional Ingredients)

The mascara composition of the present invention may further include various additives desirably used in cosmetic or dermatological compositions. For example, water, dispersants, anti-oxidants, pH adjusters, preservatives, neutralizing agents, fragrances, fillers, film formers, co-solvents, waxes, plasticizers, cosmetic and dermatological active agents such as emollients, moisturizers, vitamins, UV filters, and sunscreens, and mixtures thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

The combination of the olefin/acrylate grafted polymer and the acrylates copolymer may render optional the inclusion of film formers such as polymers. In a preferred embodiment, the mascara composition includes no polymer other than the olefin/acrylate grafted polymer and the acrylates copolymer. Nonetheless, the mascara compositions may include other polymers, such as film forming polymers, provided that they are compatible with the other ingredients in the inventive compositions and do not substantially, adversely affect the advantageous properties of the mascara composition. If present, the amount of the polymer(s) other than the olefin/acrylate grafted polymer and the acrylates copolymer is less than about 20% by weight, preferably less than about 10% by weight, relative to the total weight of the mascara composition.

The mascara composition of the present invention may be in any form suitable for applying on keratinous materials, in particular keratin fibers. For example, the mascara composition may be an emulsion (a water-in-oil emulsion, oil-in-water emulsion, multiple emulsion such as W/O/W and O/W/O, or nanoemulsion), a non-emulsified mixture of a water phase and an oil phase, an oil-free composition, or a water-free composition.

According to preferred embodiments, the mascara composition of the present invention is in the form of an emulsion. The mascara composition may be a water-in-oil emulsion, an oil-in-water emulsion, a multiple emulsion such as W/O/W and O/W/O, or a nanoemulsion.

The mascara composition of the present invention is intended to be applied onto keratinous materials such as keratin fibers, in particular, eyelashes or eyebrows.

According to some embodiments of the present invention, the mascara composition may have a texture suitable to be applied onto keratinous materials. The texture may be evaluated, for example, by measuring viscosity or thickness of the mascara composition. The texture may also be evaluated by experienced researchers by checking dragging properties or tackiness of the mascara composition.

Preferably, after the mascara composition is applied onto keratinous materials, the mascara composition is allowed to dry before subjecting to contact with other objects such as clothing and skin. According to one embodiment of the present invention, the mascara composition dries within a sufficiently short time for making up keratin fibers such as eyelashes and eyebrows. Depending on the amount of the mascara composition applied onto the keratinous materials, the mascara composition may completely dry within about 15 minutes, preferably about 10 minutes, more preferably about 5 minutes, after the application. As used herein, the mascara composition is considered "completely dried" when the mascara composition is not transferred to other objects upon contacting therewith.

According to preferred embodiments of the present invention, the mascara composition may have long-lasting properties and thus may stay on keratinous materials such as keratin fibers for a sufficient amount of time without changing, or without substantially changing, its appearance. For example, the mascara composition may stay on the keratin fibers without breaking, cracking, flaking, smudging, and/or smearing for about 6 hours or more, preferably about 8 hours or more, more preferably about 12 hours or more, without reapplying the mascara composition onto keratin fibers. For example, the keratin fibers on which the mascara composition is applied may have a more defined appearance, desired intensity of colors, spiking appearance, and sufficient thickness, length, and/or curl, upon application, or even after about 6 hours, after about 8 hours, or preferably after about 12 hours, of application.

The mascara composition may have waterproof properties. Thus, the mascara composition may repel water when exposed to water.

As described above, according to one aspect of the present invention, the mascara composition has improved cosmetic properties such as, for example, increased volume properties, increased curling properties, increased curl retention properties, increased length properties, and/or increased long wear properties.

(Methods)

Some embodiments of the present invention relate to a method of making a mascara composition including mixing at least one olefin/acrylate grafted polymer and at least one acrylates copolymer until dissolution. The olefin/acrylate grafted polymer and the acrylates copolymer may be mixed by stirring, shaking, grounding, or beating, optionally with a stirrer, a magnetic stirrer, a shaker, a homogenizer, or any other methods suitably used to mix cosmetic composition. The mixing may be carried out with or without heating or cooling the ingredients. When mixing, the ratio of the weight amount of olefin/acrylate grafted polymer to the amount of acrylates copolymer may be: preferably about 0.85 or greater, about 1 or greater, about 1.5 or greater, and particularly preferably about 2 or greater; and preferably about 4.5 or less, preferably about 4 or less, and particularly preferably about 3 or less. Preferably, the ratio of the weight amount of the olefin/acrylate grafted polymer to the weight amount of the acrylates copolymer is from about 0.85 to about 4.5, including all ranges and subranges therebetween.

One embodiment of the present invention provides a method of improving curl of keratinous materials. The mascara composition described above is applied onto the keratinous materials. The keratinous materials are preferably keratin fibers, in particular eyelashes and eyebrows. The mascara composition is applied onto the keratinous materials in an amount sufficient to improve the curl of the keratinous materials. To improve the curl of keratin fibers, the mascara composition may be applied onto the keratin fibers in an amount sufficient to increase the curl, and also a volume and/or length of the keratin fibers.

The way by which the mascara composition is applied onto the keratinous materials is not limited. Preferably, the mascara composition is applied onto keratin fibers by a brush, a wand, or a comb.

The compositions may be applied to eyelashes as needed, preferably once or twice daily, more preferably once daily and then preferably allowed to dry before subjecting to contact such as with clothing or other objects.

According to preferred embodiments of the present invention, the mascara composition is dried by leaving the mascara composition applied onto keratinous materials for a sufficient amount of time to dry the mascara composition. The mascara composition may dry within a sufficiently short time for making up keratinous materials, in particular keratin fibers such as eyelashes and eyebrows. Depending on the amount of the mascara composition applied onto the keratinous materials, the mascara composition may completely dry within about 15 minutes, preferably about 10 minutes, more preferably about 5 minutes, after the application.

One embodiment of the present invention provides a method of enhancing appearance of eyelashes for a sufficient length of time. The mascara composition described above is applied onto the eyelashes. The mascara composition is applied onto the keratinous materials in an amount sufficient to enhance the physical appearance of eyelashes. In one embodiment, the mascara composition is applied onto the eyelashes in an amount sufficient to increase a volume, length, and/or curl of the eyelashes. After the mascara composition is applied, the eyelashes may have more defined appearance. After the application, the eyelashes may be longer, thicker and/or more curled, as compared to naked eyelashes.

One embodiment of the present invention provides a method of increasing curl of eyelashes. The mascara composition described above is applied onto the eyelashes in an amount sufficient to increase curl of the eyelashes.

Another embodiment of the present invention provides a method of maintaining curls of the eyelashes for a sufficient amount of time. In preferred embodiments of the present invention, the eyelashes may maintain their curls for about 6 hours or more, preferably about 8 hours or more, more preferably about 12 hours or more. The mascara composition may stay on the eyelashes for about 6 hours or more, preferably about 8 hours or more, more preferably about 12 hours or more.

In the above-described methods, the mascara composition of the present invention may be applied topically to the eyelashes in an amount sufficient to make up the eyelashes, or to enhance the appearance of the eyelashes.

The mascara composition of the present invention may be a waterproof mascara composition.

The following examples are intended to illustrate the invention without limiting the scope as a result. The percentages are given on a weight basis, unless indicated otherwise.

Notwithstanding that the numerical ranges and parameters setting forth the broad scope of the invention are approximations, the numerical values set forth in the specific examples are reported as precisely as possible. Any numerical value, however, inherently contain errors necessarily resulting from the standard deviation found in their respective measurements.

EXAMPLES

Mascara Compositions

Mascara compositions of Example 1 and Comparative Example 1 were prepared from the ingredients shown in Table 1 below.

TABLE 1

| | Ingredients (wt %) | Example 1 | Comparative Example 1 |
|---|---|---|---|
| A1 | DI water | 39.35 | 44.45 |
| | Plenoxyethanol | 0.50 | 0.50 |
| | Butylene glycol | 2.00 | 2.00 |
| | Sodium dehydroacetate | 0.20 | 0.20 |
| | Glycerol stearate | 6.20 | 6.20 |
| | Sodium EDTA | 0.10 | 0.10 |
| | Litium magnesium sodium silicate | 1.00 | 1.00 |
| | Dimethicone and dimethiconol | 1.00 | 1.00 |
| A2 | Aminomethyl propanedoil | 0.70 | 0.70 |
| A3 | Iron oxide black | 10.00 | 10.00 |
| B | Beeswax | 2.50 | 5.00 |
| | Carnauba wax | 1.45 | 2.89 |
| | Paraffin | 3.10 | 4.82 |
| | Stearic acid | 2.90 | 2.90 |
| | Uniclear | 1.00 | 1.00 |
| | VP eicosene copolymer | 1.00 | 1.00 |
| | Tocophenyul acetate | 0.20 | 0.20 |
| | Cetyl alcohol | 1.50 | 1.50 |
| C | Caprylyl glycol | 0.30 | 0.30 |
| D | Olefin/acrylate grafted polymer (and) sodium laureth sulphate (and) C12-15 Sec-Pareth 15 (Syntran ® EX 108) | 17.00 | 0 |

TABLE 1-continued

| Ingredients (wt %) | Example 1 | Comparative Example 1 |
|---|---|---|
| Acrylates copolymer (and) butylene glycol (and) sodium laureth sulphate (Syntran ® EX 53) | 8.00 | 0 |
| Stylene/acrylates/ammoonimu methacrylate copolymer (Syntran ® 5760 CG) | 0 | 14.24 |
| TOTAL | 100 | 100 |

The mascara compositions of Example 1 and Comparative Example 1 were prepared as follows:

1. a beaker containing Phase A1 DI water was heated in a water bath;
2. other Phase A1 to A3 ingredients were added to the beaker and mixed to ground pigments for 1 hour;
3. all Phase B ingredients were combined in a container and heated together by a water bath for up to 20 minutes until all Phase B ingredients were melt and mixed;
4. when both Phase A ingredients in 2 and Phase B ingredients in 3 reached 95° C., Phase A ingredients were added to the container of Phase B ingredients and homogenized for 20 minutes;
5. the container was removed from the water bath and cooled to 70° C. or less; and
6. Phases C and D ingredients were added to the container and mixed for up to 10 minutes.

The mascara compositions of Example 1 and Comparative Example 1 were evaluated by twelve expert panellists by applying each of the compositions on their own eyelashes. The evaluation was conducted prior to the application, during the application, 8 hours after the application, and 12 hours after the application.

For each of the mascara compositions, the panellists held a mascara wand with their dominant hand, applied 10 strokes of the mascara compositions onto their eyelashes, and dipped the mascara wand in the mascara composition. The same procedure was repeated three times, so that a total of 30 strokes of mascara composition were applied. The panellists wore the mascara compositions for over 12 hours and evaluated the appearance and the feel of the mascara composition after 8 hours and 12 hours from the application.

(i) Prior to Application

The panellists indicated that the composition of Example 1 had significantly more gloss (shininess) as compared to the composition of Comparative Example 1.

The panellists indicated that significantly more amount of the composition of Example 1 was taken on the mascara wand as compared to the composition of Comparative Example 1.

The panellists indicated that the composition of Comparative Example 1 had significantly more fragrance intensity as compared to the composition of Comparative Example 1.

(ii) During Application

The panellists indicated that eyelashes treated with the composition of Example 1 had a significantly more spiked appearance and stiffness as compared to those treated with the composition of Comparative Example 1.

(iii) 8 Hours after the Application

The panellists indicated that significantly more amount of the composition of Example 1 remained on the eyelashes as compared to the composition of Comparative Example 1.

The panellists indicated that the eyelashes treated with the composition of Example 1 had a significantly more spiked appearance (on multiple lashes) and stiffness as compared to those treated with the composition of Comparative Example 1.

(iv) 12 Hours after the Application

The panellists indicated that significantly more amount of the composition of Example 1 remained on the eyelashes as compared to the composition of Comparative Example 1.

The panellists indicated that the eyelashes treated with the composition of Example 1 had a significantly more spiked appearance (on multiple lashes) and stiffness as compared to those treated with the composition of Comparative Example 1.

The panellists indicated that the eyelashes treated with the composition of Example 1 had significantly more curls than those treated with the composition of Comparative Example 1.

Comparison of the compositions of Example 1 and Comparative Example 1 shows that the mascara composition including an olefin/acrylate grafted polymer and an acrylates copolymer provided eyelashes with improved shininess, hardness, spiking appearance, curl, and intensity. As the expert panelists indicated, the composition of Example 1 provided eyelashes with an improved spiking appearance and stiffness after 8 hours and 12 hours of wearing, as compared to Comparative Example 1. The results indicate that the shininess, spiking appearance, stiffness, curl, eyelash length, and amount of composition remaining on eyelashes, were improved by using olefin/acrylate grafted polymer and an acrylates copolymer, as compared to conventional mascara formula including relatively large amount of wax(es), while maintaining other attributes such as increased volume. By including an olefin/acrylate grafted polymer and an acrylates copolymer, such as Syntran® EX108 and Syntran® EX53, it may be possible to prepare cosmetically preferable mascara composition with smaller amount of waxes.

Mixtures of an Olefin/Acrylate Grafted Polymer and an Acrylates Copolymer

To evaluate thermal properties of compositions including an olefin/acrylate grafted polymer and an acrylates copolymer, an olefin/acrylate grafted polymer and an acrylates copolymer were mixed with various ratios. The ratios are shown in Table 2 below.

TABLE 2

| Weight ratio (Syntran® EX108:Syntran® EX 53) | Weight ratio (olefin/acrylate grafted polymer:acrylates copolymer) | (olefin/acrylate grafted polymer)/ (acrylates copolymer) | $T_g$ (° C.) |
|---|---|---|---|
| 0:1 | 100% acrylates copolymer | — | 14.83 |
| 1:3 | 22:78 | 0.28 | 11.91 |
| 1:1 | 46:54 | 0.85 | 5.22 |
| 3:1 | 71:29 | 2.45 | 2.17 |
| 5:1 | 81:19 | 4.26 | −0.66 |
| 1:0 | 100% olefin/acrylate grafted polymer | — | −5.22 |

The mixtures of Syntran® EX108 and Syntran® EX 53 with various mixing ratios were analysed with DSC Q2000 (differential scanning calorimeter), TA instrument. Each of the mixtures were cast onto a Teflon-coated petri dish and dried for a week with 25 m² air flow to form a dried film. The dried films were then heated at 10° C./min from −80° C. to 125° C. (Cycle 1), cooled at 10° C./min from 125° C. to −80° C. (Cycle 2), and heated at 10° C./min from −80° C. to 150° C. (Cycle 3). The results are shown in FIGS. 1A and 1B.

Figure 1B:
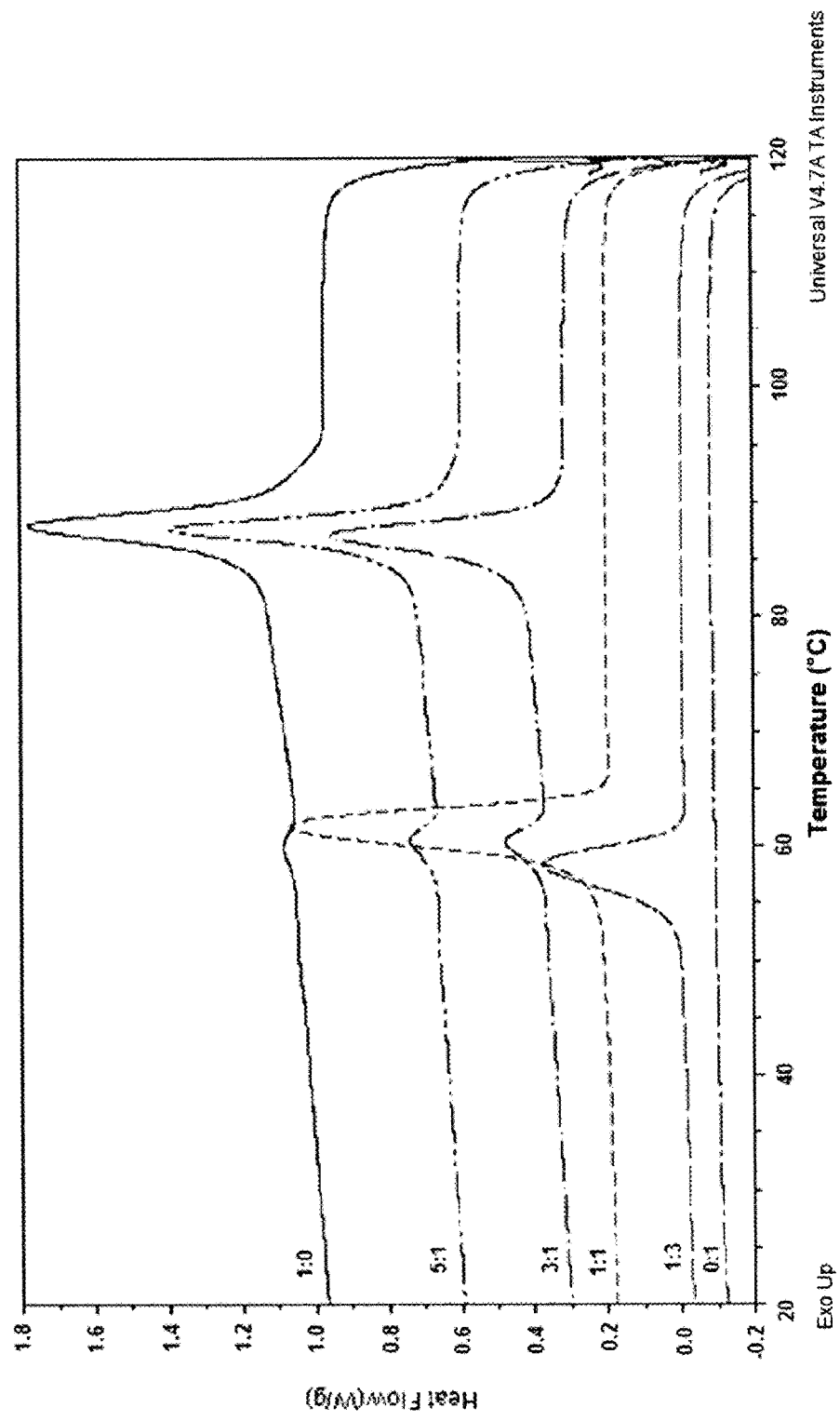
FIG. 1B is a graph showing the DSC measurement result when cooling mixtures of Syntran® EX108 and Syntran® EX 53 with various mixing ratios. The mixing ratio indicates a weight ratio of (Syntran® EX108):(Syntran® EX 53).
Figure 2:
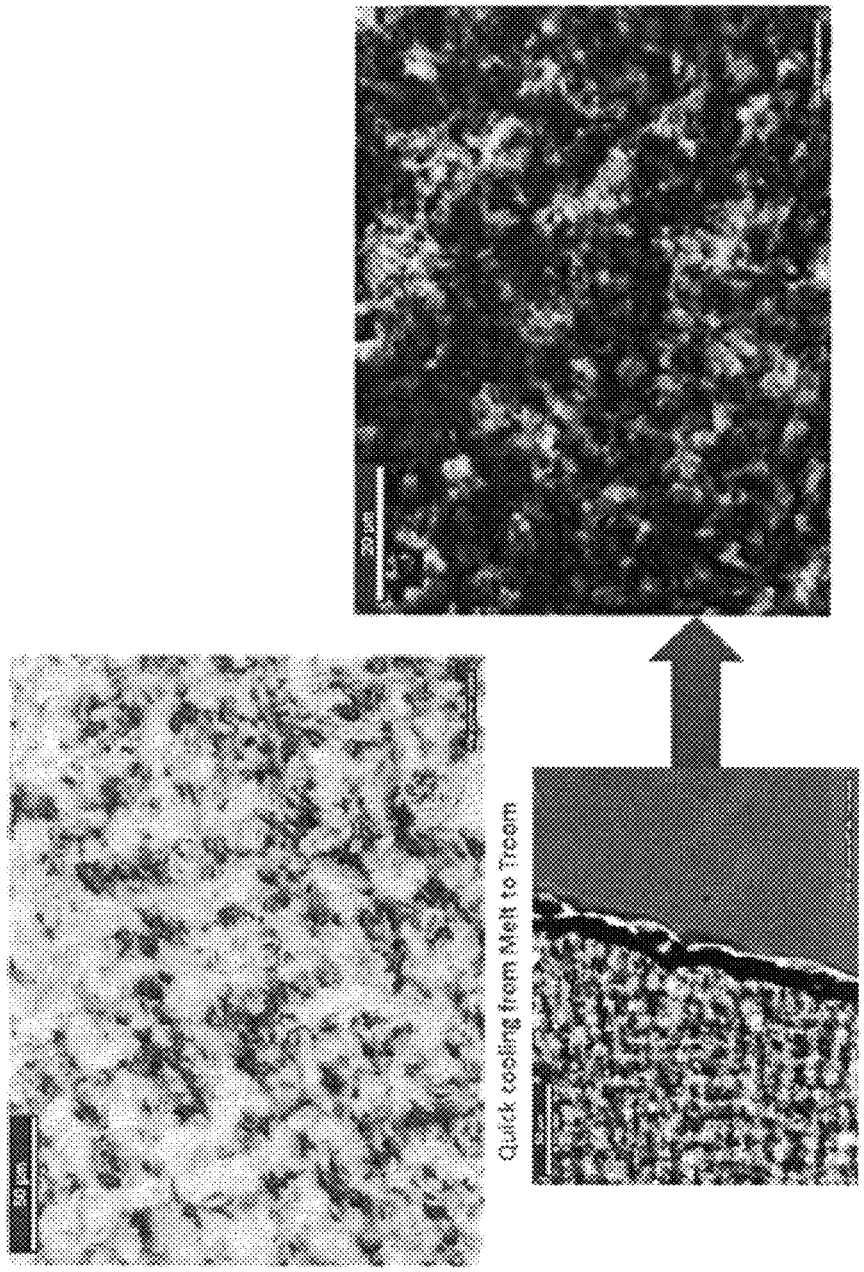
FIG. 2 shows microscopic images of crystalline structures formed by cooling Syntran® EX108 from 130° C. to 25° C. at a rate of 2° C./min.

FIGS. 1A and 1B show the thermal properties of the mixtures of Syntran® EX108 and Syntran® EX 53 with different mixing ratios. As shown in FIG. 1A, as the ratio of Syntran® EX108 in the mixture increased, the film formed by the mixture became softer and melted at a temperature of from 90 to 110° C., and the $T_g$ value decreased to below 0° C. As shown in FIG. 1B, in the mixtures of Syntran® EX 108 and Syntran® EX 53 with a ratio of 1:0, 5:1, and 3:1, the crystallization peak appeared at 80 to 90° C. upon cooling the mixtures. Such results appear to be caused by the formation of small crystals from Syntran® EX 108, as shown in FIG. 2.

Figure 3:
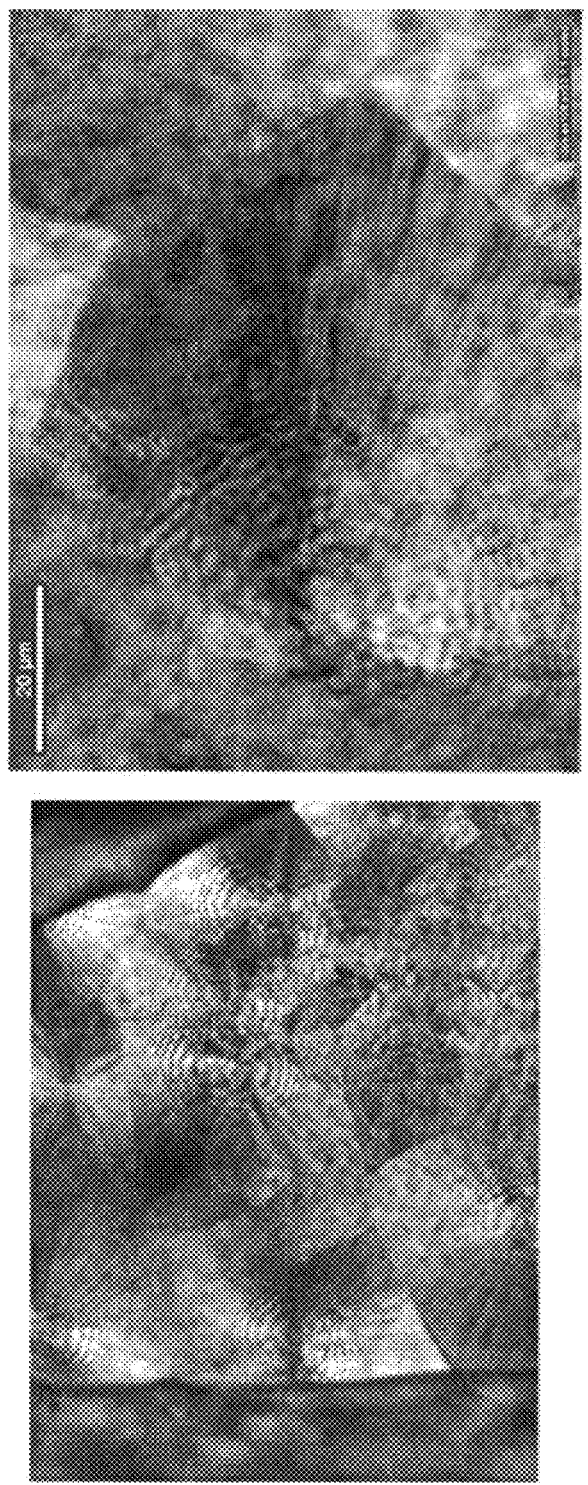
FIG. 3 shows microscopic images of crystalline structures formed from the mixture of Syntran® EX108 and Syntran® EX 53 with a mixing ratio of 1:1.

As shown in FIG. 1B, as the ratio of Syntran® EX53 in the mixture increased from 50% to 99% (in the mixtures of Syntran® EX 108 and Syntran® EX 53 with a ratio of 1:1 and 1:3), another crystallization peak at 50 to 70° C. became larger. The film prepared from pure Syntran® EX 53 (the mixture of Syntran® EX 108 and Syntran® EX 53 with a ratio of 0:1) did not show any peaks. When the amount of Syntran® EX53 was about 50% in the mixture, large crystals were formed uniformly throughout the film as seen in FIG. 3.

Figure 4:
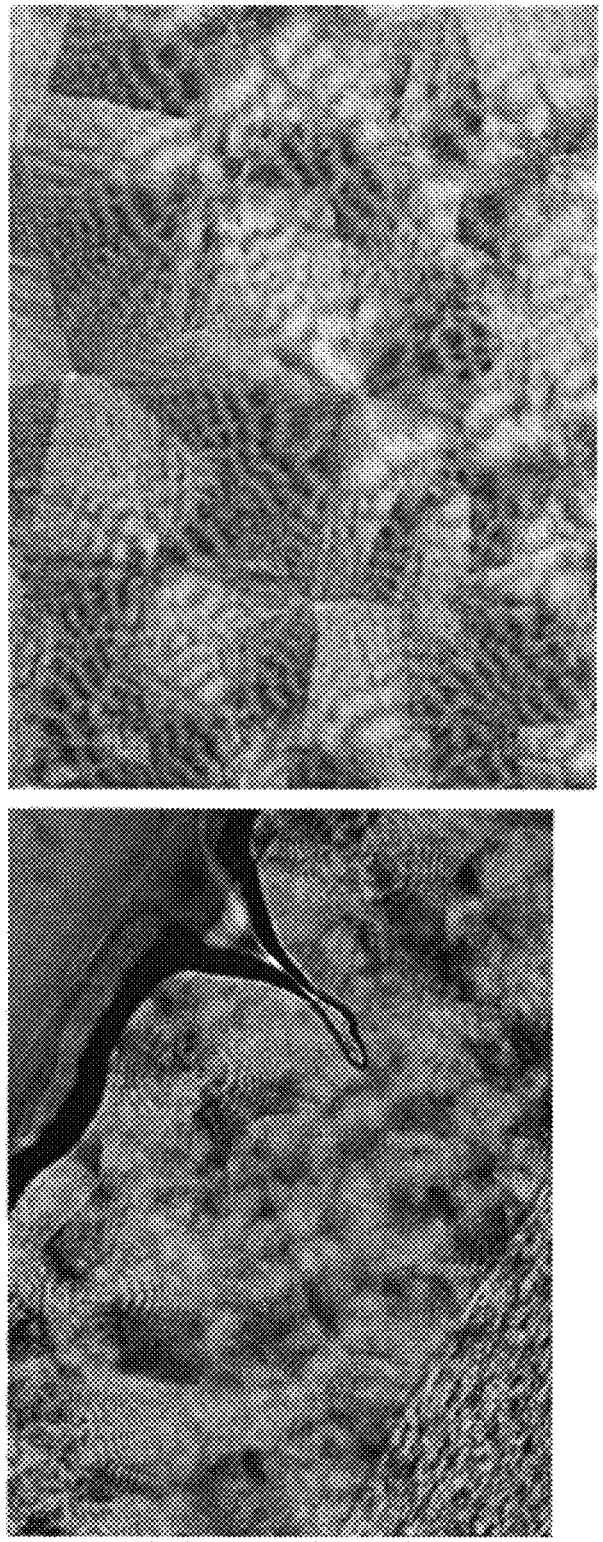
FIG. 4 shows microscopic images of crystalline structures formed from the mixture of Syntran® EX108 and Syntran® EX 53 with a mixing ratio of 3:1.

When the concentration of Syntran® EX53 in the mixture was from about 19% to less than 50% (in the mixtures of Syntran® EX 108 and Syntran® EX 53 with a ratio of 5:1 and 3:1), there were larger amount of Syntran® EX108 crystals distributed throughout the film, forming random amorphous structures. As the peak at 50 to 70° C. shown in FIG. 1B became smaller, the peak at 80 to 90° C. shown in FIG. 1B became more dominant, and the large crystals disappeared. When the mixing ratio of Syntran® EX 108 and Syntran® EX 53 was about 3:1, smaller crystals appeared throughout the film, as shown in FIG. 4. The amorphous crystal structure formed in the film may increase the hardness or stiffness of the film, improving structural integrity of the film.

The invention claimed is:

1. A mascara composition, comprising:
   at least one olefin/acrylate grafted polymer; and
   at least one acrylates copolymer,
   wherein a ratio of a weight amount of the olefin/acrylate grafted polymer to a weight amount of the acrylates copolymer in the mascara composition is from 2.45 to 4.26.

2. The mascara composition of claim 1, further comprising at least one wax.

3. The mascara composition of claim 2, wherein an amount of the wax is 10% by weight or less relative to the total weight of the mascara composition.

4. The mascara composition of claim 1, wherein
   the weight amount of the olefin/acrylate grafted polymer is from 1 to 15% relative to the total weight of the mascara composition, and
   the weight amount of the acrylates copolymer is from 1 to 10% relative to the total weight of the mascara composition.

5. The mascara composition of claim 1, wherein
   the weight amount of the olefin/acrylate grafted polymer is from 2 to 10% relative to the total weight of the mascara composition, and
   the weight amount of the acrylates copolymer is from 2 to 8% relative to the total weight of the mascara composition.

6. The mascara composition of claim 1, wherein the olefin/acrylate grafted polymer is a semi-crystalline polymer.

7. The mascara composition of claim 1, wherein the olefin/acrylate grafted polymer has a glass transition temperature of less than 0° C.

8. The mascara composition of claim 1, wherein the acrylates copolymer has a glass transition temperature of 0° C. or greater.

9. A method of increasing curl of eyelashes, comprising:
   applying a mascara composition comprising an olefin/acrylate grafted polymer and an acrylates copolymer onto eyelashes in an amount sufficient to makeup eyelashes,
   wherein a ratio of a weight amount of the olefin/acrylate grafted polymer to a weight amount of the acrylates copolymer is from 2.45 to 4.26.

10. A method of making a mascara composition, comprising
    mixing an olefin/acrylate grafted polymer and an acrylates copolymer until dissolution,
    wherein a ratio of a weight amount of the olefin/acrylate grafted polymer to a weight amount of the acrylates copolymer mixed in the mascara composition is from 2.45 to 4.26.

11. The mascara composition of claim 1, wherein the mascara composition is free from wax.

* * * * *